United States Patent [19]
Reiber

[11] Patent Number: 5,639,959
[45] Date of Patent: Jun. 17, 1997

[54] CORROSION MEASUREMENT APPARATUS AND GALVANIC COUPON AND GASKET THEREFOR

[76] Inventor: Harold Steven Reiber, 17441 - 47th Ave. NE, Seattle, Wash. 98155

[21] Appl. No.: 653,462

[22] Filed: May 24, 1996

Related U.S. Application Data

[63] Continuation of Ser. No. 396,540, Mar. 1, 1995, abandoned, which is a continuation-in-part of Ser. No. 13,460, Sep. 24, 1993, Pat. No. Des. 362,902.

[51] Int. Cl.$^6$ .................................................. G01N 17/00
[52] U.S. Cl. ............................................................ 73/86
[58] Field of Search .............................. 73/86; 277/201, 277/202, 225; 285/370, 371, 397, 417, 910

[56] References Cited

U.S. PATENT DOCUMENTS

| | | |
|---|---|---|
| D. 330,073 | 10/1992 | Valls . |
| D. 342,567 | 12/1993 | Boen . |
| 750,444 | 1/1904 | Fisher ................................ 285/371 |
| 1,876,455 | 9/1932 | Inshaw ................................ 277/225 |
| 3,236,096 | 2/1966 | Macatician et al. . |
| 3,320,570 | 5/1967 | Lied, Jr. . |
| 3,980,542 | 9/1976 | Winslow, Jr. et al. . |
| 3,996,124 | 12/1976 | Eaton et al. . |
| 4,036,591 | 7/1977 | Stanfill .................................. 73/86 |
| 4,120,313 | 10/1978 | Lewis . |
| 4,179,653 | 12/1979 | Davies et al. . |
| 4,226,693 | 10/1980 | Maes . |
| 4,330,376 | 5/1982 | Lai et al. . |
| 4,338,563 | 7/1982 | Rhoades et al. . |
| 4,468,613 | 8/1984 | Slough et al. . |
| 4,818,209 | 4/1989 | Petersson et al. . |
| 4,947,132 | 8/1990 | Charoy et al. . |
| 5,208,162 | 5/1993 | Osborne et al. ........................ 72/86 |

OTHER PUBLICATIONS

Reiber et al.; "An Improved Method for Corrosion–Rate Measurement by Weight Loss"; Nov., 1988; Journal AWWA; pp. 41–46.

HDR Engineering brochure; date unknown; "Lead and Copper Rule Corrosion Testing; Coupon Sleeve Approach to Corrosion Control Demonstration Studies".

*Primary Examiner*—Robert Raevis
*Attorney, Agent, or Firm*—Christensen O'Connor; Johnson & Kindness PLLC

[57] ABSTRACT

The present invention includes an improved gasket and coupon for use with a corrosion measurement system. The gasket includes a pair of collar portions which fit into an end of the coupon. The central rib of the gasket has a pair of beveled faces each of which fit flush with the exterior edge of a coupon when the coupon and gaskets are pressure fit into the sleeve. The central rib includes a flat outer edge that contacts the inner wall of the sleeve to stabilize the coupon within the sleeve and to prevent liquid from leaking between two adjacent gaskets. The coupon includes a first material, copper, a portion of which is coated with a second material, lead/tin, such that a galvanic cell is formed. Preferably, the lead/tin coating is placed on the interior and exterior of the upper or lower half of the coupon, the other half of the galvanic cell of the coupon remains uncoated copper. Thus, a galvanic cell more representative of the soldered pipe joint is formed allowing for more precise corrosion test results to be obtained.

20 Claims, 3 Drawing Sheets

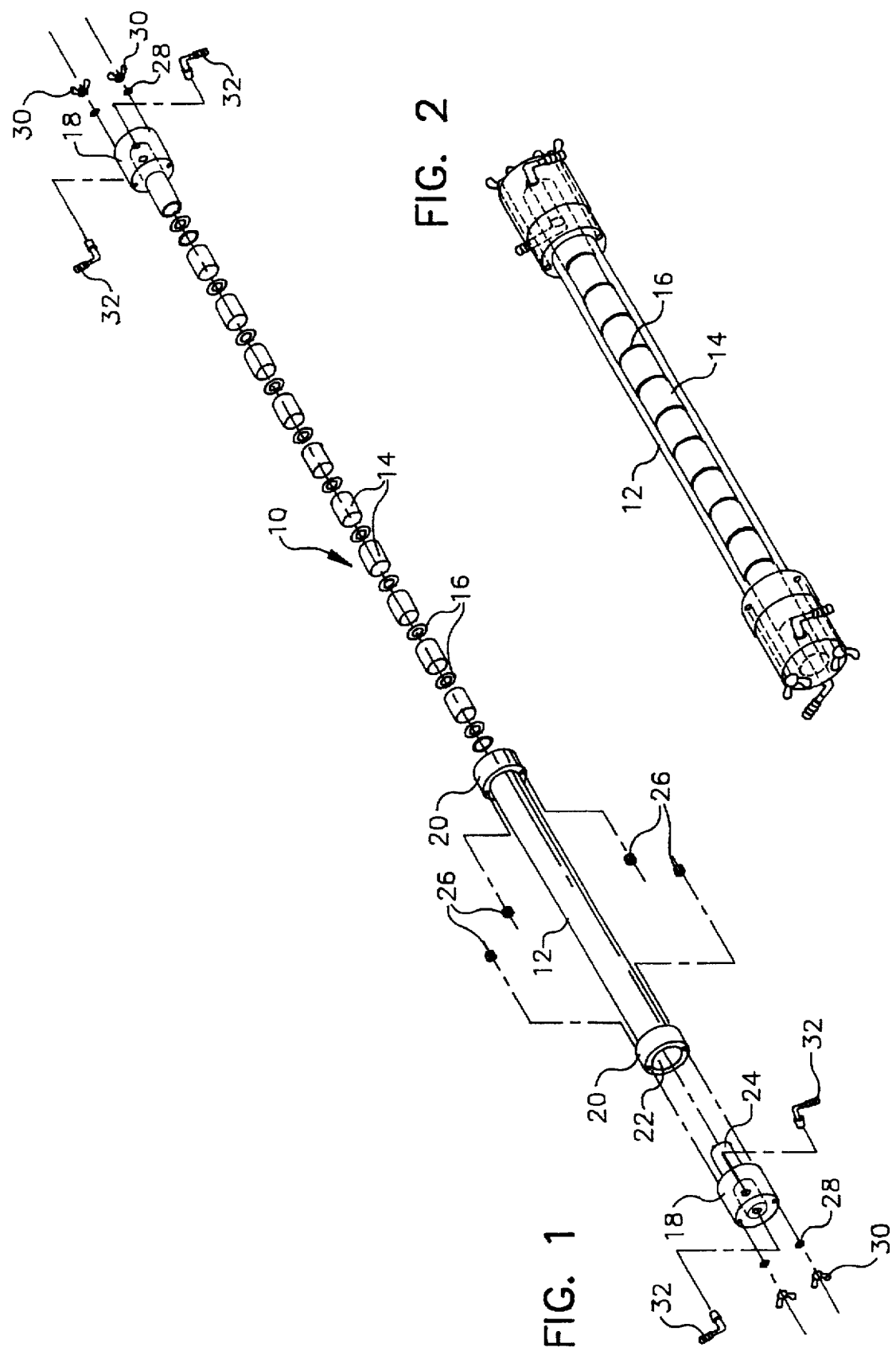

CORROSION MEASUREMENT APPARATUS AND GALVANIC COUPON AND GASKET THEREFOR

CROSS-REFERENCE TO RELATED APPLICATIONS

This application is a continuation of application Ser. No. 08/396,540, filed Mar. 1, 1995, (now abandoned), the benefit of the filing dates of which are hereby claimed under 35 USC 120, which application is a continuation-in-part of U.S. design patent application No. 29/013,460, filed Sep. 24, 1993, now U.S. Design Pat. No. 362,902.

BACKGROUND OF THE INVENTION

The present invention relates to corrosion measurement systems, and more particularly, the present invention relates to a corrosion measurement assembly for plumbing materials exposed in a drinking water environment.

DESCRIPTION OF THE PRIOR ART

There exists a variety of devices and methods for testing the amount of pipe corrosion present in a water line. Of the different corrosion-rate measurements, long-term weight loss (representing the cumulative loss of metal over an extended period of exposure) is the measurement of greatest interest in distribution networks. Such measures usually take two forms. The first and oldest is the flat coupon approach, in which a thin rectangular piece of the metal of interest is inserted on an insulating stem into the flow stream of a distribution line. The point of insertion is usually an exposed tee, elbow, or corporation stop. Although other materials can be used, the coupon is most often stamped from milled carbon sheet steel and is intended to represent the pipe wall of a black-iron service line.

The second approach is the machined-nipple test. The technique is a significant improvement because it uses actual pipe inserts as the corrosion medium. The black-iron inserts, generally of one inch diameter and four inch length are machined to fit snugly inside a PVC nipple. The exterior and ends of the pipe insert are coated with an epoxy resin to prevent corrosion on non-wetted surfaces. In operation, the nipple assembly can be plumbed into any convenient delivery line or used within a closed-loop system for laboratory testing. A particular advantage of the machined nipple is that the flow conditions within the test section reproduce the effect of pipe hydrodynamics. Thus the potential effects of impingement corrosion can be studied, and the growth and erosion of oxide films and scale on pipe walls can be duplicated.

The system components used to perform the machined-nipple test typically include a coupon sleeve consisting of four major elements: an outer sleeve, coupons disposed within the sleeve, gaskets disposed between each coupon, and headpieces at either end of the sleeve. The sleeve is made of a transparent polycarbonate plastic and serves to protect and align the coupons. The sleeve further serves to provide the structural support against which the headpieces generate the compressive force that seals the coupons against the gaskets. The transparency of the sleeve aids the coupon loading process, and allows for detection of problematic water leaks between coupons.

The coupons provide the test surfaces upon which the corrosion takes place. To make the corrosion measurement as representative of the plumbing materials as possible, the coupons are fabricated from actual tubing and piping materials. A variety of plumbing materials may be used to fabricate the coupons, including: milled steel pipe, galvanized pipe, and copper tubing or brass tubing. The interior coupon surfaces are polished (300 grit finish) to ensure a uniform and homogeneous test surface. The exterior of the coupon is coated in a phenolic resin to protect it from corrosion or damage during handling and storage.

The gaskets are known to constructed of "TEFLON" and serve to align the coupons in the sleeve and provide a water tight seal between coupons (water flow in the sleeve is restricted to the interior of the coupons).

The headpieces, and associated plunger, generate the compressive forces that seal the coupons against the "TEFLON" gaskets. The headpieces are attached to each end of the sleeve by screws that force the plunger assemblies down the bore of the sleeve compressing the coupons and gaskets between them. The headpieces also contain the tube fittings for all hydraulic connections, as well as sample ports.

Numerous innovations for corrosion testing device have been provided in the prior art that are adapted to be used. Even though these innovations may be suitable for the specific individual purposes to which they address, they would not be suitable for the purposes of the present invention as heretofore described.

SUMMARY OF THE INVENTION

The present invention includes an improved gasket and coupon for use with a corrosion measurement system. The gasket is used to ensure accurate test results by preventing water from passing between adjacent coupons and contacting the exterior of the coupons. The gasket includes a pair of collar portions which fit into an end of the coupon. The central rib of the gasket has a pair of beveled faces each of which fit flush with the exterior edge of a coupon when the coupon and gaskets are pressure fit into the sleeve. The central rib includes a flat outer edge that contacts the inner wall of the sleeve to stabilize the coupon within the sleeve and to prevent liquid from leaking between two adjacent gaskets.

The coupon is a modified coupon which measures corrosion caused by the electrochemical galvanic phenomenon associated with a solder sweated water pipe joint. The water pipe solder joint is comprised of solder (for example lead/tin) on a pipe (for example copper). The contact of these dissimilar metals causes a galvanic cell to exist, with the copper being the cathode and the solder being the anode. In this chemical reaction, the lead/tin solder is oxidized and released into the water. The modified coupon recreates this condition and consists of a coupon of a first material, copper, a portion of which is coated with a second material, lead/tin, such that a galvanic cell is formed. Preferably, the lead/tin coating is placed on the interior and exterior of the upper or lower half of the coupon, the other half of the galvanic cell of the coupon remains uncoated copper. Thus, a galvanic cell more representative of the soldered pipe joint is formed allowing for more precise corrosion test results to be obtained.

Accordingly, it is an object of the present invention to provide an improved gasket to prevent water from passing between adjacent coupons and contacting the exterior of the coupons.

Another object of the present invention is to provide an improved coupon which measures corrosion caused by the electrochemical galvanic phenomena associated with a solder sweated water pipe joint.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWING

| 10 | coupon measurement apparatus | 12 | sleeve |
|----|------------------------------|----|--------|
| 14 | coupon | 14g | galvanized coupon |
| 16 | gasket | 18 | headpiece |
| 20 | mounting ring | 22 | bore |
| 24 | plunger | 26 | bolts |
| 28 | washer | 30 | wing nut |
| 32 | ports | 52 | collar portion |
| 53 | exterior beveled edge | 54 | central rib |
| 56 | beveled faces | 58 | flat outer edge |
| 72 | copper surface | 74 | lead/tin coating |

BRIEF DESCRIPTION OF THE PREFERRED EMBODIMENT

FIG. 1 is an exploded view of the corrosion measurement apparatus of the present invention;

FIG. 2 is a perspective view of the apparatus of FIG. 1;

Figure 3:
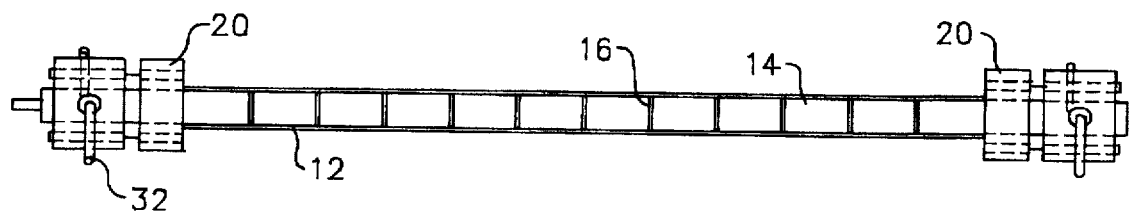
Figure 4:
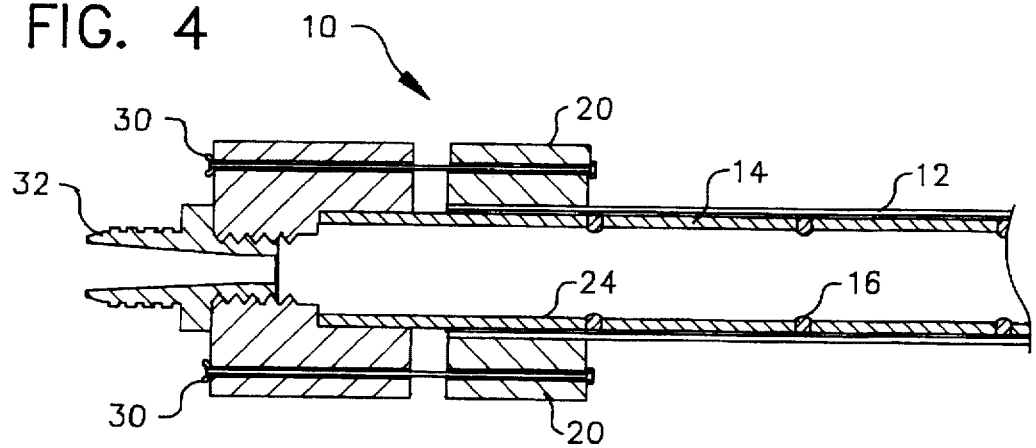
Figure 5A:
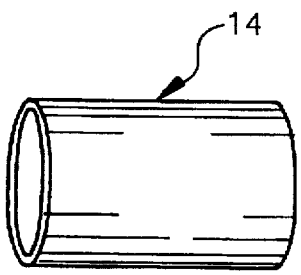
Figure 5B:
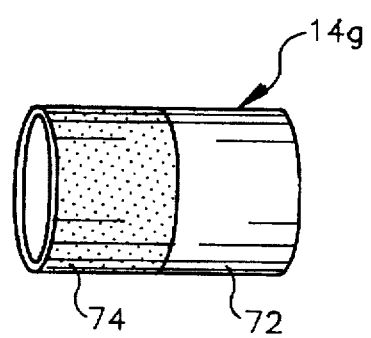
Figure 6:
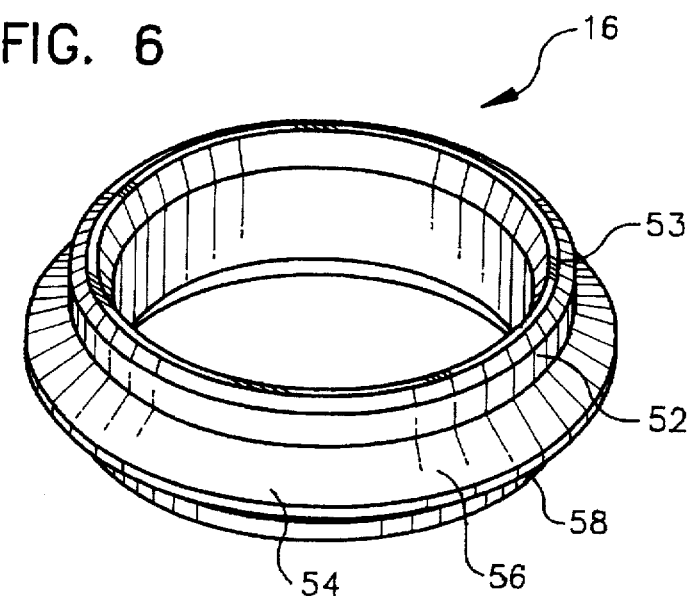
Figure 7:
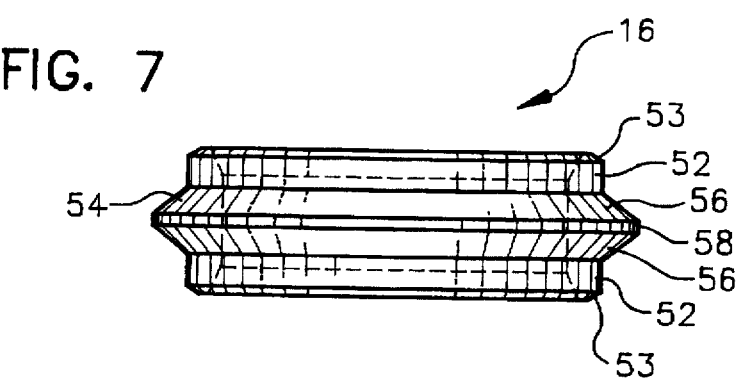
Figure 8:
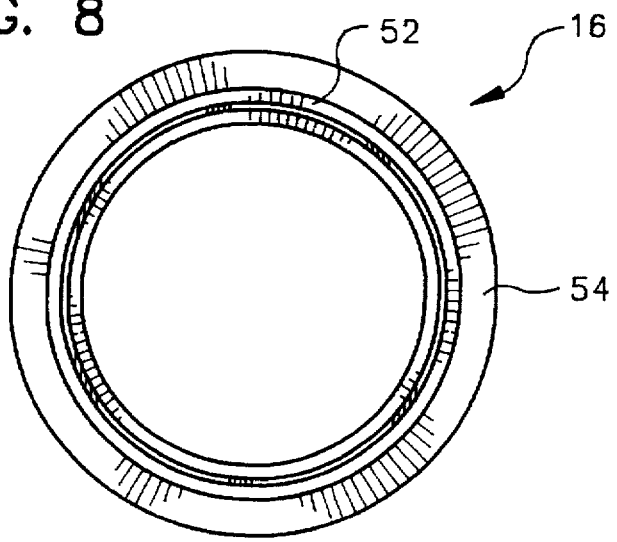

FIG. 3 a front elevational view of the apparatus of FIG. 1;

FIG. 4 a partial cross-sectional view of the apparatus of FIG. 1;

FIG. 5A is an elevational perspective view of a coupon of the apparatus of FIG. 1;

FIG. 5B is an elevational perspective view of a galvanized coupon of the apparatus of FIG. 1;

FIG. 6 is a perspective view of a gasket constructed in accordance with the present invention;

FIG. 7 is a side view of a gasket constructed in accordance with the present invention; and FIG. 8 is a top view of a gasket constructed in accordance with the present invention.

DETAILED DESCRIPTION OF THE PREFERRED EMBODIMENT

Referring initially to FIGS. 1–4, the corrosion measurement apparatus of the present invention is shown. The apparatus 10 is designed to perform the machined-nipple test and includes four major elements: an outer sleeve 12, coupons 14 disposed within the sleeve 12, gaskets 16 disposed between each coupon 14, and headpieces 18 at both ends of the sleeve 12. The sleeve 12 is made of a transparent polycarbonate plastic and serves to protect and align the coupons 14. The sleeve 12 further serves to provide the structural support against which the headpieces 18 generate the compressive force that seals the coupons 14 against the gaskets 16. The transparency of the sleeve 12 aids the coupon loading process, and allows for detection of problematic water leaks between coupons 14. At both ends of the sleeve 12 is a mounting ring 20, the sleeve 12 and mounting rings 20 defining an internal bore 22. The mounting rings 20 are adapted to engage with the headpieces 18 as described in detail below.

Referring to FIG. 5A in conjunction with FIG. 1, the coupons 14 provide the test surfaces upon which the corrosion takes place. To make the corrosion measurement as representative of the plumbing materials as possible, the coupons 14 are fabricated from actual tubing and piping materials. A variety of plumbing materials may be used to fabricate the coupons 14, including: milled steel pipe, galvanized pipe, and copper tubing or brass tubing. The interior coupon surfaces are polished (300 grit finish) to ensure a uniform and homogeneous test surface. The exterior of the coupon 14 is coated in a phenolic resin (not shown) to protect it from corrosion or damage during handling and storage.

The present invention encompasses coupons which replicate the electrochemical galvanic action occurring at the joints of solder sweated pipes, as shown in FIG. 5B. The galvanized coupon 14g consists of a copper pipe section partially coated with a lead-tin solder. The contact of the two dissimilar metals creates a galvanic cell that accelerates the corrosion process and increases the lead release rate on the solder surface. The galvanic coupon 14g is the most effective means of replicating the impact of corrosion on solder sweated joints, which is of particular importance because of the potential for substantial lead release into household plumbing systems.

More specifically, coupon 14g is a modified coupon which measures corrosion caused by the electrochemical galvanic phenomenon associated with a solder sweated water pipe joint. The water pipe solder joint is comprised of solder (for example lead/tin) on a pipe (for example copper). The contact of these dissimilar metals causes a galvanic cell to exist, with the copper being the cathode and the solder being the anode. In this chemical reaction, the lead/tin solder is oxidized and released into the water. The modified coupon recreates this condition and consists of a coupon 14g of a first material 72, for example copper, a portion of which is coated with a second material 74, for example lead/tin, such that a galvanic cell is formed. Preferably, the lead/tin coating 74 is placed on the interior and exterior of the upper or lower half of the coupon 14g, the other half of the galvanic cell of the coupon 14g remains uncoated copper Thus, a galvanic cell more representative of the soldered pipe joint is formed allowing for more precise corrosion test results to be obtained.

Referring to FIGS. 1 through 4, the gaskets 16 are preferably constructed of "TEFLON" and serve to align the coupons 14 in the sleeve 12 and provide a water tight seal between coupons 14 (water flow in the sleeve is restricted to the interior of the coupons 14). Headpieces 18, and associated plunger 24, generate the compressive forces that seal the coupons 14 against the "TEFLON" gaskets 16. The headpieces 18 are attached to each end of the sleeve 12 by bolts 26 which are threaded through the mounting rings 20 and the headpieces 18, and which are secured by washers 28 and wing nuts 30. The plunger assemblies 24 are dimensioned to fit snugly within the bore 22 in the sleeve 12 such that the plunger assemblies 24, when inserted into the bore 22 of the sleeve 12, are tightened by rotation of the wing nuts 30 to compress the coupons 14 and gaskets 16 between them. The headpieces 18 also contain the tube fittings 32 for all hydraulic connections, as well as sample ports.

Turning now to FIGS. 6 through 8, gasket 16 is shown in detail. Gasket 16 ensures accurate test results by preventing water from passing between adjacent coupons and contacting the exterior of the coupons 14. The gasket 16 includes a pair of collar portions 52, each with an exterior bevelled edge which fit into an end of the coupon 14. The central rib 54 of the gasket 16 has a pair of beveled faces 56 each of which fit flush with the exterior edge of a coupon 14 when the coupon and gaskets 16 are pressure-fit into the sleeve 12. The central rib 54 includes a flat outer edge 58 that contacts the inner wall of the sleeve 12 to stabilize the coupon 14 within the sleeve 12 and to prevent liquid from leaking between two adjacent gaskets.

While the invention has been illustrated and described as embodied in a corrosion measurement apparatus, it is not intended to be limited to the details shown, since it will be understood that various omissions, modifications, substitutions and changes in the forms and details of the device illustrated and in its operation can be made by those skilled in the art without departing in any way from the spirit of the present invention.

What is claimed as new and desired to be protected by Letters Patent is set forth in the appended claims:

1. A method for measuring galvanically induced corrosion in fluid comprising the steps of:
   a) coating a tubular body comprised of a first material with a second material electro-chemically dissimilar from said first material such that a galvanic cell is formed between said first material and said second material, said tubular body lacking welds and scratches sufficient to cause measurable corrosion by cavitation and increased surface area; and
   b) introducing said tubular body into an electrolytic fluid such that a galvanic cell is formed and galvanic activity occurs for a predetermined length of time, said first material containing copper and said second material being solder.

2. The method of claim 1 further comprising the step of:
   c) measuring the physical changes in said first material and said second material caused by at least the galvanic activity in the fluid.

3. The method of claim 2, wherein said step of measuring includes determining the change in mass of said first material and said second material.

4. The method of claim 1, wherein said electrolytic fluid is water.

5. The method of claim 4, wherein said solder is a lead-tin alloy.

6. The method of claim 1, wherein said coating is applied to approximately one half of the surface area of said tubular member.

7. A method for measuring galvanically induced corrosion in fluid of a tubular galvanic cell having a first end and a second end and having an anode on said first end and a cathode on said second end, the method comprising the steps of:
   a) mating about one half of a tubular body comprised of a first material with a second material electro-chemically dissimilar from said first material such that a galvanic cell is formed between said first material and said second material, said tubular body lacking welds and scratches sufficient to cause measurable corrosion by cavitation and increased surface area; and
   b) introducing said tubular body into an electrolytic fluid such that a galvanic cell is formed and galvanic activity occurs for a predetermined length of time, said first material containing copper and said second material being solder.

8. The method of claim 7, wherein said electrolytic fluid is water.

9. The method of claim 8, wherein said solder is a lead-tin alloy.

10. A method for measuring galvanically induced corrosion in fluid comprising the steps of:
   a) coating a tubular body comprised of a first material with a second material electro-chemically dissimilar from said first material such that a galvanic cell is formed between said first material and said second material, said tubular body lacking welds and scratches sufficient to cause measurable corrosion by cavitation and increased surface area;
   b) introducing said tubular body into an electrolytic fluid such that a galvanic cell is formed and galvanic activity occurs for a predetermined length of time; and
   c) measuring the physical changes in said first material and said second material by at least the galvanic activity in the fluid, said first material containing copper and said second material being solder.

11. The method of claim 10, wherein said fluid is water.

12. The method of claim 11, wherein said solder is a lead-tin alloy.

13. The method of claim 10, wherein said coating is applied to approximately one half of the surface area of said tubular member.

14. The method of claim 10, wherein said step of measuring includes determining the change in mass of said first material and said second material.

15. A method for measuring galvanically induced corrosion in fluid comprising the steps of:
   a) coating a tubular body comprised of a first material with a second material electro-chemically dissimilar from said first material such that a galvanic cell is formed between said first material and said second material, said tubular body lacking welds and scratches sufficient to cause measurable corrosion by cavitation and increased surface area; and
   b) introducing said tubular body into an electrolytic fluid such that a galvanic cell is formed and galvanic activity occurs for a predetermined length of time, said first material containing copper.

16. The method of claim 15 further comprising the step of:
   c) measuring the physical changes in said first material and said second material caused by at least the galvanic activity in the fluid.

17. The method of claim 15, wherein said second material is solder and said electrolytic fluid is water.

18. A method for measuring galvanically induced corrosion in fluid comprising the steps of:
   a) coating a tubular body comprised of a first material with a second material electro-chemically dissimilar from said first material such that a galvanic cell is formed between said first material and said second material, said tubular body lacking welds and scratches sufficient to cause measurable corrosion by cavitation and increased surface area; and
   b) introducing said tubular body into an electrolytic fluid such that a galvanic cell is formed and galvanic activity occurs for a predetermined length of time, said second material being solder.

19. The method of claim 18, further comprising the step of:
   c) measuring the physical changes in said first material and said second material caused by at least the galvanic activity in the fluid.

20. The method of claim 18, wherein said first material is copper and said electrolytic fluid is water.

* * * * *

UNITED STATES PATENT AND TRADEMARK OFFICE
CERTIFICATE OF CORRECTION

PATENT NO. : 5,639,959
DATED : June 17, 1997
INVENTOR(S) : H.S. Reiber

It is certified that error appears in the above-indentified patent and that said Letters Patent is hereby corrected as shown below:

| COLUMN | LINE | |
|---|---|---|
| Title page, | *Attorney, Agent, or Firm* | After "O'Connor" delete ";" |
| 5 (Claim 7, | 50 line 6) | "mating" should read --coating-- |

Signed and Sealed this

Twenty-third Day of September, 1997

Attest:

Attesting Officer

BRUCE LEHMAN

Commissioner of Patents and Trademarks